United States Patent
Alvarez Diez et al.

(10) Patent No.: US 10,942,375 B2
(45) Date of Patent: Mar. 9, 2021

(54) DEVICE FOR DETERMINING CENTRING PARAMETERS FOR THE ADJUSTMENT OF SPECTACLES

(71) Applicants: Carl Zeiss Vision International GmbH, Aalen (DE); Carl Zeiss AG, Oberkochen (DE)

(72) Inventors: Cristina Alvarez Diez, Oberkochen (DE); Tobias Breuninger, Riederich (DE); Michael Gamperling, Leipheim (DE); Oliver Schwarz, Ellwangen (DE); Frank Widulle, Neu-Ulm (DE)

(73) Assignees: Carl Zeiss Vision International GmbH, Aalen (DE); Carl Zeiss AG, Oberkochen (DE)

( * ) Notice: Subject to any disclaimer, the term of this patent is extended or adjusted under 35 U.S.C. 154(b) by 0 days.

(21) Appl. No.: 16/523,027

(22) Filed: Jul. 26, 2019

(65) Prior Publication Data
US 2020/0073151 A1    Mar. 5, 2020

Related U.S. Application Data

(63) Continuation of application No. PCT/EP2018/051873, filed on Jan. 25, 2018.

(30) Foreign Application Priority Data

Jan. 27, 2017 (EP) .................................... 17153556

(51) Int. Cl.
*A61B 3/10* (2006.01)
*G02C 13/00* (2006.01)
(Continued)

(52) U.S. Cl.
CPC ............ *G02C 13/005* (2013.01); *A61B 3/111* (2013.01); *G03B 17/48* (2013.01); *G03B 17/561* (2013.01)

(58) Field of Classification Search
CPC .... G02C 5/126; G02C 13/003; G02C 13/005; G03B 17/48; G03B 17/561; G03B 35/04;
(Continued)

(56) References Cited

U.S. PATENT DOCUMENTS 7,384,144 B2   6/2008   Ross-Messemer et al.
7,740,355 B2   6/2010   Sessner et al.
(Continued)

FOREIGN PATENT DOCUMENTS

EP    1038495 A2    9/2000
EP    1704437 B1    7/2015
(Continued)

OTHER PUBLICATIONS

Hartley et al.: "Multiple View Geometry in Computer Vision," 2nd edition, pp. 1 to 8, Cambridge University Press 2004.
(Continued)

*Primary Examiner* — Mustak Choudhury
(74) *Attorney, Agent, or Firm* — Thrive IP®; Georg M. Hasselmann (57) ABSTRACT

A device for determining centering parameters for the adjustment of spectacles includes a camera support partially surrounding an inner area that is open at the top, bottom and to the rear; and at least three cameras arranged between two free ends of the camera support and pointing towards the inner area, the camera support having an illumination system in order to illuminate the inner area. The illumination system is designed to light the inner area such that the light intensity, at least at each point in a region extending over a height of 20 cm and a central angle of 180 degrees of an outer cylinder surface having a diameter of 20 cm and formed in the inner area, deviates by a maximum +50% and −30% from a predefined desired value.

27 Claims, 3 Drawing Sheets

(51) Int. Cl.
  *A61B 3/11*   (2006.01)
  *G03B 17/48*  (2021.01)
  *G03B 17/56*  (2021.01)

(58) Field of Classification Search
  CPC .... G03B 35/08; G03B 35/126; G06K 7/1096; G06K 7/10722; G06K 7/10732; G06K 7/10752; G06K 2207/1018; A61B 3/111; A61B 5/70; A61B 5/1114
  See application file for complete search history.

(56) References Cited

U.S. PATENT DOCUMENTS

| | | | |
|---|---|---|---|
| 9,395,562 | B1 | 7/2016 | Nguyen et al. |
| 2003/0081173 | A1 | 5/2003 | Dreher |
| 2007/0285528 | A1 | 12/2007 | Mise et al. |
| 2009/0051871 | A1* | 2/2009 | Warden .................. G02C 5/126 351/204 |
| 2010/0239135 | A1* | 9/2010 | Luisi ...................... G03B 35/08 382/128 |
| 2015/0304530 | A1 | 10/2015 | Courteille et al. |

FOREIGN PATENT DOCUMENTS

| | | |
|---|---|---|
| EP | 1844363 B2 | 12/2015 |
| EP | 3012687 A1 | 4/2016 |
| FR | 3024911 A1 | 2/2016 |
| WO | 2005033793 A1 | 4/2005 |

OTHER PUBLICATIONS

DIN EN ISO 13666 (Ophthalmic optics—Spectacle lenses), dated Oct. 2013.
Extended European Search Report issued in EP 17153556.0, to which this application claims priority, dated Jul. 6, 2017.
International search report issued in international application PCT/EP2018/051873, to which this application claims priority, and English-language translation thereof, dated Aug. 22, 2018.
International preliminary examination report issued in international application PCT/EP2018/051873, to which this application claims priority, dated May 2, 2019, and English-language translation thereof.
Office action by the Chinese Intellectual Property Office issued in CN 201880022415.5, which is a counterpart hereof, dated May 7, 2020, and English-language translation thereof.

\* cited by examiner

DEVICE FOR DETERMINING CENTRING PARAMETERS FOR THE ADJUSTMENT OF SPECTACLES

CROSS REFERENCE TO RELATED APPLICATIONS

This application is a continuation application of international application PCT/EP2018/074346, filed Jan. 25, 2018, which claims priority to European patent application EP 17153556.0, filed Jan. 27, 2017, both of which are hereby incorporated by reference in their entireties.

TECHNICAL FIELD

The disclosure relates to an apparatus having a camera carrier, which carries at least three cameras and an illumination device, and to a method for determining centration parameters for the adjustment of spectacles.

BACKGROUND

Centration parameters are used to correctly arrange or center spectacle lenses in a spectacle frame such that the spectacle lenses are arranged at the correct position relative to the eyes of the person wearing the spectacles. Here, these are in part anatomical parameters of the relevant person such as the interpupillary distance, in part purely frame-specific parameters such as the lens width or the lens height, and in part combinations of anatomical and frame-specific parameters, such as the vertex distance and the fitting point height. An overview of conventional centration parameters is provided by DIN EN ISO 13666, dated October 2013.

Apparatuses with which automatic determination of centration parameters is possible are known. For example, EP 1 844 363 B2 discloses such an apparatus in which images of a person wearing spectacles or a spectacle frame are recorded using two cameras from different viewing directions, such that centration parameters can be determined from the recorded image data. US 2010/0239135 A1 discloses an apparatus having a plurality of image capturing device modules, which serves to examine children with plagiocephalism and does not determine centration parameters.

However, in known apparatuses for determining centration parameters, a problem that often arises is that the images recorded from different viewing directions fluctuate in terms of quality and utilizability.

SUMMARY

It is therefore an object of the disclosure to refine an apparatus of the type mentioned in the introductory part in a manner such that better images of the person for which the centration parameters are to be determined can be produced.

This object is achieved according to the disclosure by an apparatus having a camera carrier, which partly encloses an interior that is open to the top, to the bottom and to a rear side, and which carries at least three cameras, which are arranged between two free ends of the camera carrier and directed into the interior, wherein the camera carrier has an illumination device for illuminating the interior, and also by corresponding methods of recording the head of a subject wearing spectacles from at least three recording directions, wherein the head of the subject is illuminated. Advantageous developments of the disclosure are discussed below.

Proceeding from US 2010/0239135, an exemplary embodiment achieves the object of attaining better lighting of the head of a subject with an illumination device set up to light the interior such that the light intensity deviates at least at every point of a region extending over a height of 20 cm and a central angle of 180 degrees of a lateral face of a cylinder, arranged in the interior, with 20 cm diameter, by at most +50% and −30% from a specified target value of 1000 lux, an exemplary embodiment achieves the object of being able to better place a subject in the interior by providing a distance sensor for measuring the distance of the head of a subject arranged in the interior, and an exemplary embodiment achieves the object of making it possible for an optician to determine centration parameters without having available a database with geometric parameters of spectacles and spectacle frames by providing a computational device that is set up to determine a three-dimensional depth profile of at least part of the head.

According to the disclosure, the apparatus has a camera carrier that partially encloses an interior but leaves it open at the top, at the bottom, and at a rear side. A subject can then move into the interior from the rear side. The interior is delimited by the camera carrier at the front and at the sides. The cameras are pointed at the interior. They are arranged in a camera arrangement extending between two free ends of the camera carrier. A concave curvature of the camera carrier typically extends in the same direction in which the camera arrangement extends between the free ends. It is possible here to provide a continuous and concave curvature, for example to give the camera carrier an arcuate form in plan view or to provide an angular outline such that the camera carrier has a front part and side parts that project from the front part at an angle. The cameras of the camera arrangement can all be arranged at the same level in a camera row or be offset vertically from one another. In order to light the interior well, the camera carrier has an illumination device that extends typically between the free ends over a length that corresponds to at least the length of the camera arrangement measured in a circumferential direction between the free ends. The illumination device expediently has at least one light strip or light-emitting means row having a multiplicity of light-emitting means. The light-emitting means are arranged in one or more rows. The at least one light strip with its multiplicity of light-emitting means, which are typically embodied in the form of LEDs, to a great extent makes uniform lighting of the interior onto which the cameras are pointed possible. According to the disclosure, the illumination device is configured such that the light intensity that is measured on a predetermined surface in the interior, specifically in a region of a lateral face of a cylinder, arranged centrally in the interior, with a diameter d of 20 cm, extending over a height h of 20 cm and a central angle α of 180 degrees, deviates at every point on the surface by at most +50% and −30% from a specified base value. The latter is for example 1000 lux, which is considered to be sufficient lighting. The illumination device can be set up here such that the light intensity exceeds a specified minimum value at every point of the specified region and then does not have to necessarily be controlled in closed-loop fashion in particular in dependence on ambient light. The homogeneity of the light in the interior is further improved if the light-emitting means emit their light into the interior through at least one large-area window 100. Reflections in the pupils, if they occur at all, are then very weak and hardly disturb the centration measurement. All light-emitting means additionally typically have a substantially uniform color temperature of approx. 4000 K+/−1000 K.

To further improve the lighting of the interior, it is typical that the illumination device has a first light strip arranged above the camera arrangement and a second light strip arranged below the camera arrangement. It is further typical that the first and the second light strip are connected to one another in each case near the free ends of the camera carrier by vertically extending further light strips. The camera arrangement is then surrounded on all sides on the inner face of the camera carrier by the light-emitting means of the light strips which typically extend over a central angle of at least 180 degrees. The distance of the upper light strip from the lower light strip is typically selected such that the aforementioned homogeneity of the light with the deviation of at most +50% and −30% from the base value is given in a region having a height of approx. 20 cm. The vertically extending further light strips or light-emitting means rows increase the light intensity in the region of the ends of the first and the second light strip or light-emitting means row, where no light is incident beyond the ends.

To be able to produce meaningful image data, it is typical that the arrangement of the cameras extends over a central angle of at least 150 degrees or that the optical axes of the cameras located closest to the free end of the camera carrier enclose an angle of at least 150 degrees. In that case it is possible to record images of the subject not only substantially from the front but also from the two sides. In addition, it is typical that the free ends of the camera carrier are located at a distance of at least 20 cm and typically of at least 25 cm from one another. A subject with a head of average width can then comfortably move into the interior from the rear side.

The camera arrangement expediently has an odd number of cameras, with one centrally arranged frontal camera and side cameras that are arranged symmetrically with respect to a plane of symmetry extending through the optical axis of the frontal camera. The more cameras the camera arrangement contains, the more accurately the centration parameters can be determined.

With particularity, an open-loop or closed-loop control device is provided for automatically or manually controlling the light intensity of the light-emitting means in dependence on the brightness in the interior and typically in dependence on the brightness that is detected using the cameras. It is typical here that sectors of the illumination device and/or individual light-emitting means are controllable separately from one another by open-loop or closed-loop control. This takes into account the fact that, in practice, stray light is routinely incident on the subject, for example through a window of the room in which the apparatus is located. To ensure uniform lighting of the subject, it may therefore be necessary for example to less strongly light the facial half that is near the window while lighting the facial half that is remote from the window all the more strongly.

According to a further advantageous refinement or alternative configuration of the disclosure, a distance sensor is provided that serves for measuring the distance of the head of the subject to the center of the camera carrier. In addition, a display unit for indicating the distance or a variable characterizing the distance is provided. In this way, positioning at the desired location, for example in the center of the interior, is made easier for the subject. While the subject can usually perform positioning in the optical axis of the frontal camera arranged in the center of the camera carrier with sufficient accuracy themselves, they can typically only poorly estimate the distance from the center of the camera carrier. The distance sensor ascertains the distance and indicates to the subject whether they are positioned too far to the front, too far to the back or correctly. An additional distance sensor can be provided here, or some of the cameras form the distance sensor such that they record the subject from different angles and determine the distance using a suitable distance measurement technique. In addition, the display unit can be configured as an additional unit and indicate for example the distance as a distance value on a display or in different colors using light-emitting means. In the latter case, it is possible to arrange, on both sides of a green light-emitting means that lights up with correct positioning, in each case a for example yellow and/or orange and/or red light-emitting means that then indicates, by lighting up, a respectively lesser or greater deviation from the correct positioning to the front or back. This type of display is highly effective. However, it is typical that the display unit is formed by the illumination device. The latter can be set up such that it changes the color of the emitted light in dependence on the distance of the head from the center of the camera carrier and, starting from pure white light that indicates correct positioning, mixes in an increasing amount of colored light. It is also possible that, if the subject is positioned incorrectly, the illumination device produces by way of local intensity or color changes a chasing light pattern that indicates the direction in which the subject is to move for correct positioning.

A fixation device for producing a fixation pattern for the subject is commonly arranged on the camera carrier, typically a fixation device that produces a speckle pattern as the fixation pattern. Such a fixation device is described in detail in EP 1 704 437 B1, which is expressly referred to in this context.

At least one of the following centration parameters is expediently determined: vertex distance of at least one eye, visual point through the plane of the spectacle lens for at least one eye, distance between the pupils, distance of at least one of the pupils from a plane of symmetry of the spectacles or the spectacle frame, location of the lens rims with respect to at least one pupil, tilt of the frame planes with respect to the vertical (pantoscopic angle). The method according to the disclosure can be simplified by the spectacle rims being approximated by boxes, defined by a box length, and a box height.

The centration data, determined according to the disclosure, may commonly be used for centering a spectacle lens in a spectacle frame and/or for grinding a spectacle lens into a spectacle frame. Here, the at least one spectacle lens is centered in the spectacle frame using the determined centration parameters in one method step or the at least one spectacle lens is ground for an arrangement in the spectacle frame on the basis of the determined centration parameters. In this way, it is possible to produce spectacle lenses and spectacles.

BRIEF DESCRIPTION OF THE DRAWINGS

Below, the disclosure will be explained in more detail on the basis of an exemplary embodiment that is depicted schematically in the drawing. In the figures.

DESCRIPTION OF EXEMPLARY EMBODIMENTS

Figure 1A:
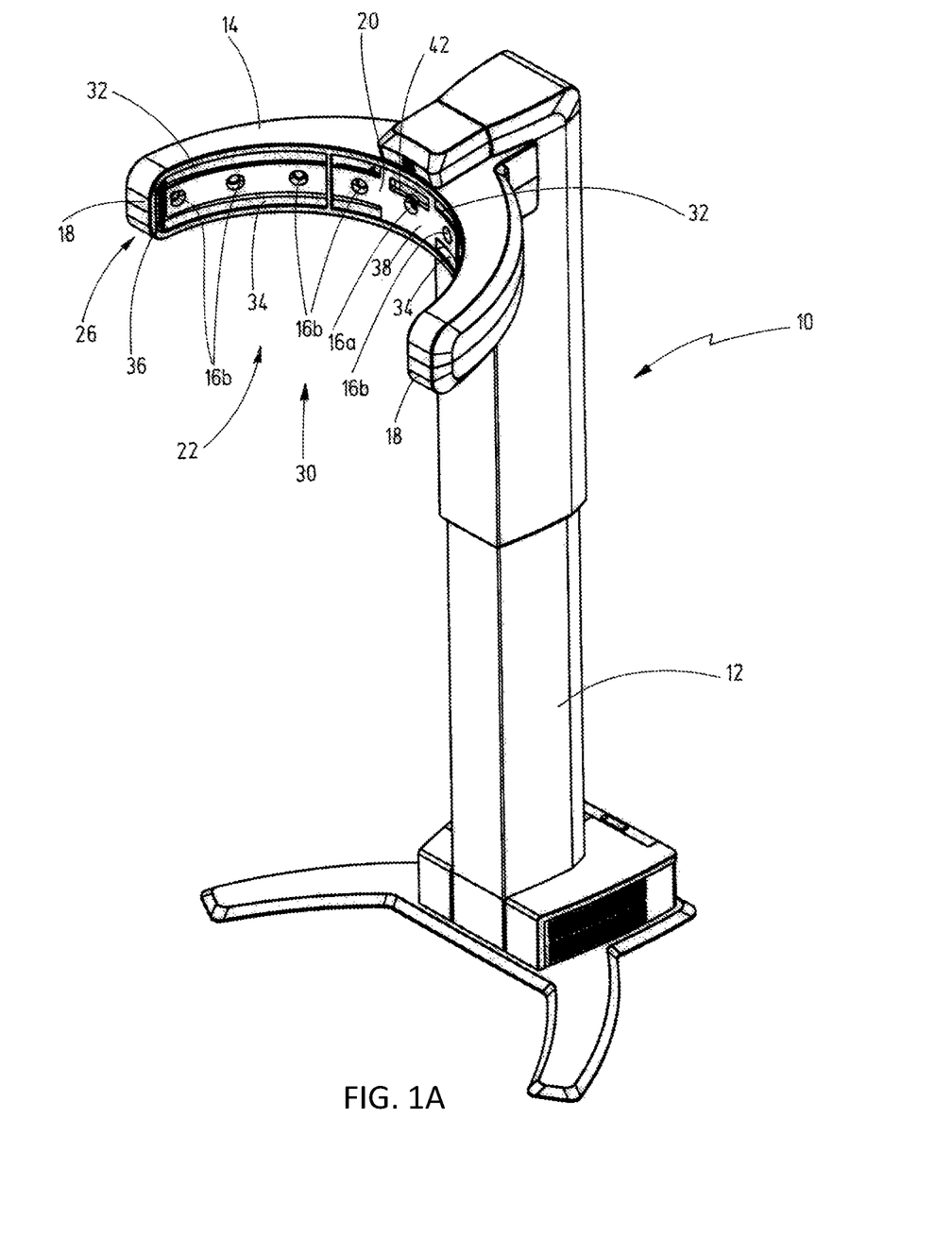
FIG. 1A shows an apparatus for determining centration parameters in a perspective view.
Figure 1B:
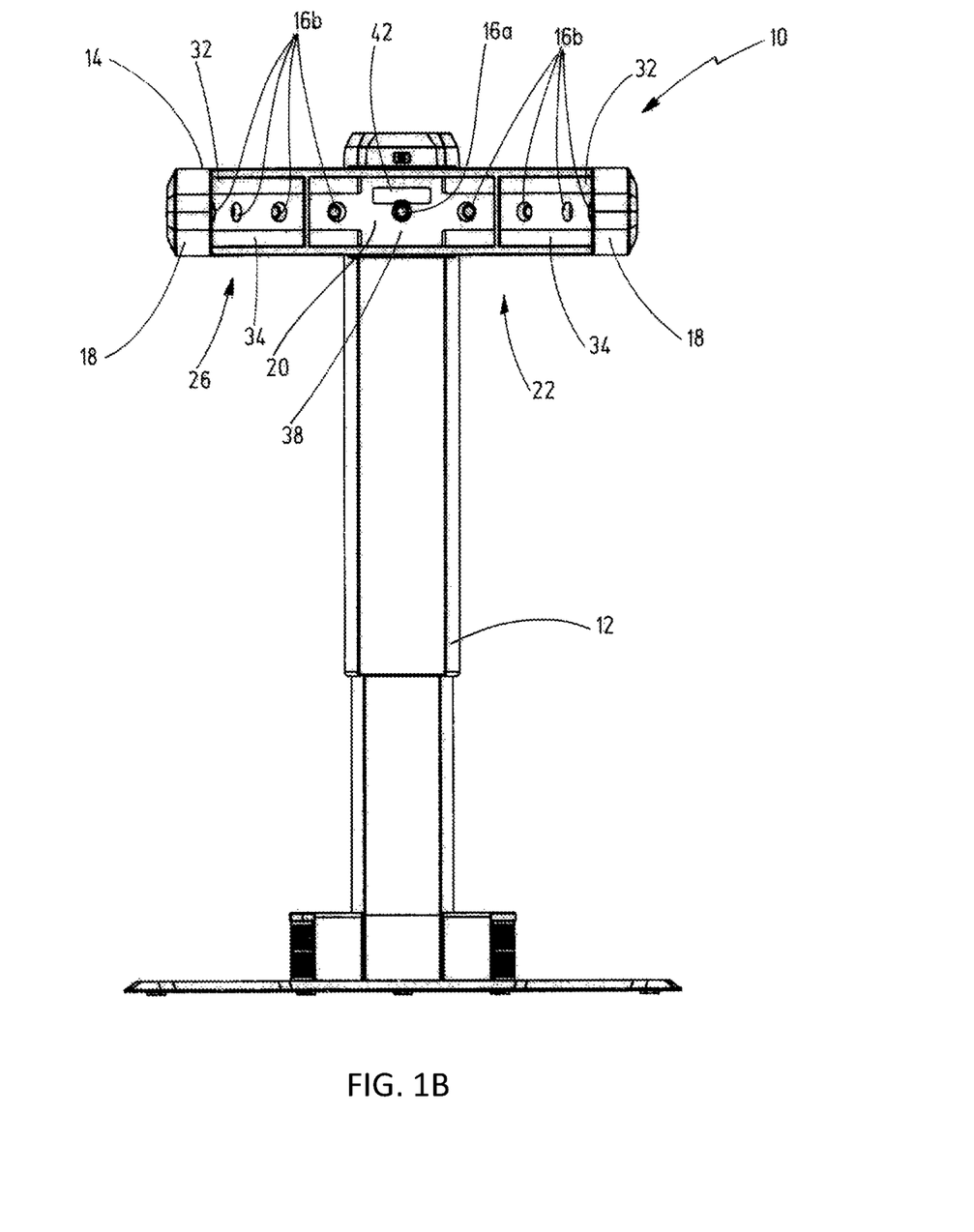
FIG. 1B shows an apparatus for determining centration parameters in a front view.
Figure 2:
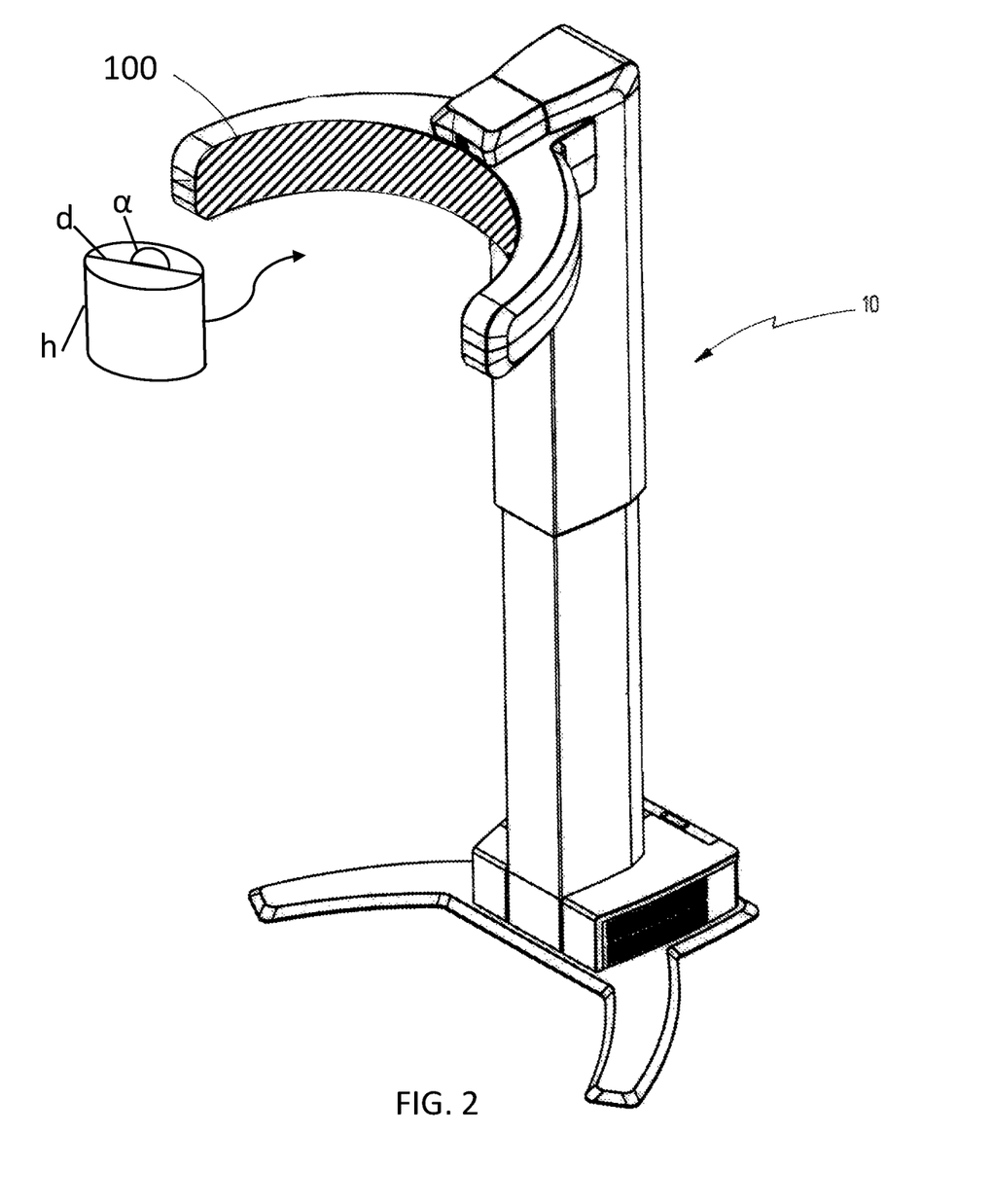
FIG. 2 shows the illumination apparatus with a large-area window.

The apparatus 10 illustrated in the drawing serves to determine centration parameters for fitting spectacles. It has a column 12 which, in a height-adjustable manner, carries a rigid camera carrier 14 which, in turn, carries a number of cameras 16a, 16b. In a plan view, the camera carrier 14 is bent into an approximately circular shape and it extends between two free ends 18 which are arranged at a distance from one another. An inner face 20 of the camera carrier 14 encloses an interior 22, in which the head of a subject is situated when images are recorded by the cameras 16a, 16b, to the front, i.e., toward the column 12, and to the sides. In a direction extending between the free ends 18, the inner face 20 is bent in a concave manner and it has, for example, the form of a portion of a lateral face of a cylinder, wherein the cylinder may have a circular or oval base. A lifting device, not illustrated in any more detail, is arranged in the column 12 for allowing the camera carrier 14 to be positioned at the correct height in relation to the head of the subject, it being possible to move the camera carrier 14 up and down in a motor-driven manner by way of the lifting device.

All cameras 16a, 16b are arranged equiangularly in a camera arrangement 26 that extends between the free ends 18. In the present exemplary embodiment, the camera arrangement 26 is embodied as a camera row 26, the cameras 16a, 16b of which are all situated at the same height, with their optical axes being directed into the interior 22. In the present exemplary embodiment, the camera row 26 comprises a frontal camera 16a arranged in the center of the camera carrier 14, the optical axis of the frontal camera being directed frontally onto the face of the subject, and eight lateral cameras 16b that are arranged symmetrically in pairs in respect of a perpendicular plane of symmetry extending through the optical axis of the frontal camera 16a, four of the lateral cameras being directed onto the face of the subject from the left and four being directed onto the face of the subject from the right in each case. Moreover, the cameras 16a, 16b are calibrated in such a way that they are able to record calibrated images of the subject at the same time. The calibration comprises the extrinsic properties, such as the relative alignment of their optical axes and the relative arrangement with respect to one another in space, and their intrinsic properties, i.e., the properties of the cameras themselves, which define how a point in space, which is situated in the internal coordinate system of the respective camera, is mapped onto the coordinates of the pixels of the recorded image. A detailed description of the calibration of cameras is found in the textbook entitled "Multiple View Geometry in Computer Vision" by Richard Hartley and Andrew Zisserman, 2nd edition, Cambridge University Press 2004, and, in particular, on page 8 therein.

The camera carrier 14 only encloses the interior 22 to the front, toward the column 12, and to the sides, i.e., to the left and right of the head of the subject. Toward the top, the bottom and toward a rear side 30, the interior is open, wherein the free ends 18 have a distance from one another of at least 25 cm such that the subject can comfortably approach from the rear side. In the exemplary embodiment shown, the distance is 70 to 80 cm, and the cameras 16a, 16b are arranged at the same angular distances with respect to one another.

In order to illuminate the interior 22, provision is made of an illumination device having an upper light strip 32 extending above the camera row 26 and a lower light strip 34 extending below the camera row 26, the light strips having a multiplicity of LEDs as light-emitting means in each case. The upper light strip 32 and the lower light strip 34 each extend, continuously or with interruptions, over a length which is at least as long as the length of the length of the camera row 26 as measured in the circumferential direction between the free ends 18. This corresponds to a circumferential angle of at least 160 degrees. Near the free ends 18, the upper light strip 32 and the lower light strip 34 are connected to one another, in each case by means of a further light strip 36 that extends in the vertical direction. Consequently, the camera row 26 is framed in the entirety thereof by at least one row of LEDs. The apparatus 10 moreover has an open-loop or closed-loop control device, not illustrated in any more detail in the drawing, by means of which the light intensity emitted by the LEDs can be controlled or regulated depending on the light intensity detected by the cameras 16a, 16b. Here, the LEDs of the light strips 32, 34, 36 are combined into sectors, the emitted light intensities of which can be controlled or regulated separately from one another. Moreover, provision is made for the light intensities emitted by the individual LEDs to also be able to be controlled or regulated separately from one another by means of the open-loop or closed-loop control device.

In order to be able to correctly position the subject in the interior 22, the two lateral cameras 16b closest to the frontal camera 16a are configured to measure the distance of the head of the subject from the center 38 of the camera carrier 14. The subject is shown whether or not they are standing correctly by means of a display unit, which is not illustrated in any more detail. The display unit has a plurality of differently colored light sources arranged in a row. The central light source lights up green when the subject stands correctly. Proceeding from the central light source, there is, in this sequence, a yellow, an orange, and a red light source in each direction, the light sources indicating, in accordance with their color, if the subject is slightly, clearly or much too far away from the center 38 of the camera carrier 14 or if the subject stands slightly, clearly or much too close to the center 38. In order to ensure that the viewing direction of the subject is directed to infinity when determining the centration parameters, a fixation device 42 arranged at the camera carrier 14 is provided, the fixation device producing a fixation pattern in the form of a speckle pattern for the subject. The fixation pattern is arranged slightly higher than the frontal camera 16a so that the subject peers over the latter. In this way, their face can be recorded to the greatest possible extent.

The apparatus 10 is also suited, in particular, to produce an avatar of the head of the subject, which may be used for determining the centration parameters. To this end, calibrated images of the head of the subject without spectacles or spectacle frame are recorded by the cameras 16a, 16b. It is common in that case when the images are recorded at the same time. A three-dimensional depth profile of the head, which images the latter very well as an approximation, is created by means of a suitable process for a geometric determination of position, such as e.g. triangulation, stereo reconstruction, multiview reconstruction, or structure from motion. The head is imaged by a multiplicity of points which can be connected to one another by means of a mesh pattern or be stored as a point cloud. In the subsequent determination of the centration parameters, the avatar thus ascertained may be used to determine centration parameters which cannot be determined, or can only be determined approximately, on account of the geometric properties of the spectacles or the spectacle frame worn by the subject. By way of example, a wide frame side may cover the eye in a lateral recording to such an extent that the vertex distance cannot be determined or can only be determined very inaccurately. Moreover, tinted or strongly reflecting lenses may not allow the eyes to be identified, or only be identified very poorly. In order to counteract this, the depth profile of the avatar is projected onto the images, recorded by the cameras 16a, 16b, of the subject wearing the spectacles or spectacle frame and the centration parameters, which can only be determined very unsatisfactorily on account of the sight being restricted by the spectacles or spectacle frame, are determined by means of the image data of the avatar. Here, for the purposes of minimizing deviations, the avatar may be adapted to the images of the subject wearing the spectacles or spectacle frame. The avatar can also be used to virtually try on spectacles or spectacle frames by way of the data describing the geometry thereof being superimposed onto the avatar.

Exemplary embodiments of the disclosure are reproduced in the following clauses:

Clause 1. Apparatus for determining centration parameters for the adjustment of spectacles, comprising a camera carrier (14), which partly encloses an interior (22) that is open to the top, to the bottom and to a rear side (30) and which carries at least three cameras (16a, 16b) which are arranged between two free ends (18) of the camera carrier (14) and directed onto the interior (22), wherein the camera carrier (14) has an illumination device (32, 34, 36) for illuminating the interior (22).

Clause 2. Apparatus according to clause 1, characterized in that the cameras are arranged in a camera arrangement (26) extending between the free ends (18) of the camera carrier (14) and in that the illumination device (32, 34, 36) extends between the free ends (18) over a length that corresponds to at least the length of the camera arrangement (26).

Clause 3. Apparatus according to clause 2, characterized in that the illumination device (32, 34, 36) has at least one light strip or a light-emitting means row having a multiplicity of light-emitting means.

Clause 4. Apparatus according to clause 3, characterized in that the illumination device has a first light strip (32) or light-emitting means row arranged above the camera arrangement (26) and a second light strip (34) or light-emitting means row arranged below the camera arrangement (26).

Clause 5. Apparatus according to clause 4, characterized in that the illumination device has further vertically extending light strips (36) or light-emitting rows that connect the first and the second light strip (32, 34) or light-emitting means row in each case close to the free ends (18).

Clause 6. Apparatus according to one of the preceding clauses, characterized in that the arrangement of the cameras (16a, 16b) extends over a central angle of at least 150 degrees and/or in that the optical axes of the cameras (16b) located closest to the free ends (18) of the camera carrier (14) enclose an angle of 150 degrees.

Clause 7. Apparatus according to one of the preceding clauses, characterized in that the free ends (18) of the camera carrier (14) are arranged at a distance of at least 25 cm in relation to one another.

Clause 8. Apparatus according to one of the preceding clauses, characterized by an open-loop or closed-loop control device for controlling the light intensity of the light-emitting means in dependence on the brightness in the interior (22).

Clause 9. Apparatus according to clause 8, characterized in that sectors of the illumination device (32, 34, 36) and/or individual light-emitting means are controllable separately from one another by open-loop or closed-loop control.

Clause 10. Apparatus according to one of the preceding clauses, characterized by a distance sensor for measuring the distance of the head of a subject from the center of the camera carrier (14) and also a display unit for indicating the distance.

Clause 11. Method for adjusting spectacles, wherein at least three calibrated first images of the head of a subject without spectacles, recorded from different perspectives, are provided, wherein a three-dimensional depth profile of at least part of the head is determined from the first images using a process for a geometric determination of position and is stored.

Clause 12. Apparatus according to clause 11, characterized in that at least one second image of the head wearing spectacles or a spectacle frame is recorded, wherein the depth profile is projected onto the at least one second image and wherein centration parameters are determined from image data of the at least one second image and from data of the depth profile projected onto the at least one second image.

Clause 13. Apparatus according to clause 11 or 12, characterized in that the projection of the depth profile onto the at least one second image is adapted to the at least one second image using an optimization process for minimizing deviations.

Clause 14. Computer program having program code for carrying out all method steps according to one of clauses 11 to 13 when the computer program is loaded on a computer and/or executed on a computer.

Clause 15. Use of an apparatus (10) according to one of clauses 1 to 11 for carrying out the method according to one of clauses 11 to 13.

Clause 16. Method for determining centration parameters for the adjustment of spectacles, wherein the head of a subject wearing spectacles is recorded from at least three recording directions and wherein the head of the subject is illuminated such that the illuminance at every point of the head that is recorded deviates from a specified target value by at most +50% and −30%.

Clause 17. Method for determining centration parameters for the adjustment of spectacles according to clause 16 using an apparatus according to one of clauses 1 to 11, characterized in that the illumination device (32, 34, 36) lights the interior (20) such that the light intensity deviates at every point of a predetermined region of a lateral face of a cylinder, arranged in the interior (22), with 20 cm diameter, by at most +50% and −30% from a specified base value.

Clause 18. Apparatus for determining centration parameters for the adjustment of spectacles, comprising at least three cameras (16a, 16b) which are calibrated with respect to one another and arranged in relation to one another such that they can record in each case an image of the head of a subject wearing spectacles at the same time and comprising a computational device that is set up to determine a three-dimensional depth profile of at least part of the head from the images using a process for a geometric determination of position.

The invention claimed is:

1. An apparatus for determining centration parameters, the apparatus comprising:
   a camera carrier configured to partly enclose an interior of the apparatus that is open to a top side, to a bottom side, and to a rear side;
   at least three cameras being are arranged between two free ends of the camera carrier and respectively directed toward the interior of the apparatus;
   an illumination device arranged on the camera carrier and being configured to illuminate the interior, wherein the illumination device is configured to illuminate a cylindrical region within the interior of the apparatus with a light intensity that deviates from a specified target value of 1000 lux by at most +50% or at most −30% for at least at every point of the cylindrical region extending over a height of 20 cm and a central angle of 180 degrees of a lateral face of the cylindrical region, the cylindrical region being arranged in the interior of the apparatus and having a diameter of 20 cm; and an open-loop or closed-loop control device configured to control the light intensity of the light emitted by the illumination device in dependence on a brightness in the interior of the apparatus to compensate for a varying strength of incident stray light, wherein the illumination device comprises at least one of a light strip or a multiplicity of light-emitting diodes arranged in a row.

2. The apparatus as claimed in claim 1, wherein the light intensity of the illumination device exceeds a specified minimum value at every point of the cylindrical region.

3. The apparatus as claimed in claim 1, wherein the at least three cameras are arranged in a camera arrangement extending between the free ends of the camera carrier, and
wherein the illumination device extends between the free ends of the camera carrier over a length that corresponds to at least a length of the camera arrangement.

4. The apparatus as claimed in claim 3, wherein the at least one of the light strip or the multiplicity of light-emitting diodes arranged in the row is arranged above the camera arrangement, and the illumination device further comprises at least one of the light strip or the multiplicity of light-emitting diodes arranged in the row arranged below the camera arrangement.

5. The apparatus as claimed in claim 4, wherein the illumination device further comprises vertically extending light strips or light-emitting diodes arranged in rows that connect the light strip or the multiplicity of light-emitting diodes arranged above the camera arrangement and the light strip or the multiplicity of light-emitting diodes arranged below the camera arrangement in each case in a proximity of the free ends.

6. The apparatus as claimed in claim 1, wherein at least one of:
the at least three cameras are arranged in an arrangement extending over a central angle of at least 150 degrees, or
optical axes of the two cameras respectively located closest to the free ends of the camera carrier enclose an angle of at least 150 degrees.

7. The apparatus as claimed in claim 1, wherein the free ends of the camera carrier are arranged at a distance of at least 25 cm in relation to one another.

8. The apparatus as claimed in claim 1, wherein sectors of the illumination device are configured to be separately controllable from one another by open-loop or closed-loop control.

9. The apparatus as claimed in claim 1 further comprising:
a distance sensor configured to measure a distance of the head of a subject from a center of the camera carrier; and
a display unit configured to indicate the distance or a variable representing the distance.

10. The apparatus as claimed in claim 1, wherein the at least three cameras are configured to respectively record first images of the head of a subject without spectacles from different perspectives and to record at least one second image of the head wearing spectacles or a spectacle frame,
the apparatus further comprising a computational device configured to:
determine a three-dimensional depth profile of at least part of the head from the first images with a process for a geometric determination of position,
store the three-dimensional depth profile,
project the three-dimensional depth profile onto the at least one second image, and
determine centration parameters from image data of the at least one second image and from data of the depth profile projected onto the at least one second image.

11. An apparatus for determining centration parameters, the apparatus comprising:
a camera carrier configured to partly enclose an interior of the apparatus that is open to a top side, to a bottom side, and to a rear side;
at least three cameras being are arranged between two free ends of the camera carrier and respectively directed toward the interior of the apparatus;
an illumination device arranged on the camera carrier and being configured to emit light to illuminate the interior,
wherein the illumination device is further configured to illuminate a cylindrical region within the interior of the apparatus with a light intensity that deviates from a specified target value of 1000 lux by at most +50% or at most −30% for at least at every point of the cylindrical region extending over a height of 20 cm and a central angle of 180 degrees of a lateral face of the cylindrical region, the cylindrical region being arranged in the interior of the apparatus and having a diameter of 20 cm;
at least one large-area window arranged to transmit the light emitted by the illumination device into the interior of the apparatus,
wherein the at least one large-area window is configured to increase a homogeneity of the light; and
an open-loop or closed-loop control device configured to control the light intensity of the light emitted by the illumination device in dependence on a brightness in the interior of the apparatus to compensate for a varying strength of incident stray light,
wherein the illumination device comprises at least one of a light strip or a multiplicity of light-emitting diodes arranged in a row.

12. An apparatus for determining centration parameters, the apparatus comprising:
a camera carrier configured to partly enclose an interior of the apparatus that is open to a top side, to a bottom side, and to a rear side;
at least three cameras being are arranged between two free ends of the camera carrier and respectively directed toward the interior of the apparatus;
an illumination device arranged on the camera carrier and being configured to illuminate the interior,
wherein the illumination device is configured to illuminate a cylindrical region within the interior of the apparatus with a light intensity that deviates from a specified target value of 1000 lux by at most +50% or at most −30% for at least at every point of the cylindrical region extending over a height of 20 cm and a central angle of 180 degrees of a lateral face of the cylindrical region, the cylindrical region being arranged in the interior of the apparatus and having a diameter of 20 cm, and wherein the at least three cameras are arranged in a camera arrangement extending between the free ends of the camera carrier, and wherein the illumination device extends between the free ends of the camera carrier over a length that corresponds to at least a length of the camera arrangement; and an open-loop or closed-loop control device configured to control the light intensity of the light emitted by the illumination device in dependence on a brightness in the interior of the apparatus to compensate for a varying strength of incident stray light.

13. An apparatus for determining centration parameters, the apparatus comprising:
a camera carrier configured to partly enclose an interior of the apparatus that is open to a top side, to a bottom side, and to a rear side;
at least three cameras being are arranged between two free ends of the camera carrier and respectively directed toward the interior of the apparatus;
an illumination device arranged on the camera carrier and being configured to illuminate the interior;
a distance sensor configured to measure a distance of the head of a subject from a center of the camera carrier; and
a display unit arranged in the illumination device and being configured to indicate the distance or a variable representing the distance,
wherein the display unit is configured to at least one of: emit light and to change a color of the emitted light, or produce a chasing light pattern in dependence on the distance of the head from the center of the camera carrier.

14. An apparatus for determining centration parameters, the apparatus comprising:
a camera carrier configured to partly enclose an interior of the apparatus that is open to a top side, to a bottom side, and to a rear side;
at least three cameras being are arranged between two free ends of the camera carrier and respectively directed toward the interior of the apparatus;
an illumination device arranged on the camera carrier and being configured to illuminate the interior,
wherein the at least three cameras are configured to respectively record from different perspectives first images of the head of a subject and at least one second image of the head wearing spectacles or a spectacle frame; and
a computational device configured to:
determine a three-dimensional depth profile of at least part of the head from the first images with a process for a geometric determination of position,
store the three-dimensional depth profile,
project the three-dimensional depth profile onto the at least one second image, and
determine centration parameters from image data of the at least one second image and from data of the depth profile projected onto the at least one second image,
wherein the illumination device comprises at least one of a light strip or a multiplicity of light-emitting diodes arranged in a row.

15. An apparatus for determining centration parameters, the apparatus comprising: a computational device configured to provide at least three calibrated first images of a head of a subject without spectacles, recorded from different perspectives; the computational device configured to determine a depth profile of at least part of the head from the first images with a process for a geometric determination of position and for storing the depth profile; and the computational device configured to provide at least one second image of the head wearing spectacles or a spectacle frame, wherein the computational device configured to determine the depth profile is further configured to project the depth profile onto the at least one second image and to determine centration parameters from image data of the at least one second image and from data of the depth profile projected onto the at least one second image, and wherein an illumination device arranged on a camera carrier comprises at least one of a light strip or a multiplicity of light-emitting diodes arranged in a row to a rear side.

16. A method for determining centration parameters, the method comprising:
illuminating a head of a subject with an illumination device;
recording the illuminated head of the subject wearing spectacles from at least three recording directions;
measuring a location of the head with respect to the at least three recording directions;
providing an indicator representing the location of the head;
displaying a distance or the indicator representing the distance with the illumination device,
providing at least three calibrated first images of the head of a subject without spectacles recorded from different perspectives;
determining a three-dimensional depth profile of at least part of the head from the first images with a process for a geometric determination of position; and
storing the three-dimensional depth profile.

17. The method as claimed in claim 16, wherein the distance or the indicator representing the distance is indicated by a color of the light emitted by the illumination.

18. The method as claimed in claim 16, further comprising:
recording at least one second image of the head wearing spectacles or a spectacle frame, wherein the depth profile is projected onto the at least one second image and wherein centration parameters are determined from image data of the at least one second image and from data of the depth profile projected onto the at least one second image.

19. The method as claimed in claim 16, wherein the process for geometric determination of position comprises triangulation.

20. The method as claimed in claim 16, wherein at least one of the following centration parameters is determined:
a vertex distance of at least one eye,
a visual point through a plane of a spectacle lens for at least one eye,
a distance between pupils,
a distance of at least one of the pupils from a plane of symmetry of the spectacles or the spectacle frame,
a location of the lens rims with respect to the at least one of the pupils, and
a pantoscopic angle.

21. The method as claimed in claim 20 further comprising:
approximating a volume occupied by the spectacle lens by a box having a box length and a box height.

22. A computer program stored on a non-transitory storage medium and having program code for carrying out the method as claimed in claim 16 when the computer program is loaded on a computer and/or executed on the computer.

23. A method for centering at least one spectacle lens in a spectacle frame, the method comprising:

determining the centration parameters with the method as claimed in claim 16; and centering the at least one spectacle lens with the determine centration parameters in the spectacle frame.

24. A method for grinding at least one spectacle lens into a spectacle frame, the method comprising:

determining the centration parameters with the method as claimed in claim 16; and grinding the at least one spectacle lens for an arrangement in the spectacle frame on the basis of the determined centration parameters.

25. A method for producing a spectacle lens, the method comprising:

grinding the spectacle lens into a spectacle frame according to the method as claimed in claim 24.

26. A method for producing a pair of spectacles, the method comprising:

producing at least one spectacle lens with the method as claimed in claim 25.

27. A method for determining centration parameters, the method comprising:

providing at least three calibrated first images of the head of a subject without spectacles recorded from different perspectives;

determining a three-dimensional depth profile of at least part of the head from the first images with a process for a geometric determination of position;

storing the three-dimensional depth profile;

recording at least one second image of the head wearing spectacles or a spectacle frame;

projecting the depth profile onto the at least one second image;

determining the centration parameters from image data of the at least one second image and from data of the depth profile projected onto the at least one second image, and adapting the projection of the depth profile onto the at least one second image to the at least one second image with an optimization process for minimizing deviations of light intensity.

\* \* \* \* \*

UNITED STATES PATENT AND TRADEMARK OFFICE
CERTIFICATE OF CORRECTION

PATENT NO.          : 10,942,375 B2                               Page 1 of 1
APPLICATION NO.     : 16/523027
DATED               : March 9, 2021
INVENTOR(S)         : Cristina Alvarez Diez et al.

It is certified that error appears in the above-identified patent and that said Letters Patent is hereby corrected as shown below:

In the Claims

Column 8, Line 63, Claim 1, change "being are" to -- being --.

Column 10, Line 20, Claim 11, change "being are" to -- being --.

Column 10, Line 53, Claim 12, change "being are" to -- being --.

Column 11, Line 17, Claim 13, change "being are" to -- being --.

Column 11, Line 38, Claim 14, change "being are" to -- being --.

Signed and Sealed this
First Day of June, 2021

Drew Hirshfeld
*Performing the Functions and Duties of the
Under Secretary of Commerce for Intellectual Property and
Director of the United States Patent and Trademark Office*